US005783570A

United States Patent [19]
Yokota et al.

[11] Patent Number: 5,783,570
[45] Date of Patent: Jul. 21, 1998

[54] ORGANIC SOLVENT-SOLUBLE MUCOPOLYSACCHARIDE, ANTIBACTERIAL ANTITHROMBOGENIC COMPOSITION AND MEDICAL MATERIAL

[75] Inventors: Hideyuki Yokota; Masakazu Tanaka; Masahiro Seko; Noriko Monden; Susumu Arimori; Shigeji Konagaya, all of Ohtsu, Japan

[73] Assignee: Toyo Boseki Kabushiki Kaisha, Osaka, Japan

[21] Appl. No.: 774,288

[22] Filed: Dec. 23, 1996

[30] Foreign Application Priority Data

| Dec. 26, 1995 | [JP] | Japan | 7-339263 |
| Jan. 8, 1996 | [JP] | Japan | 8-000954 |
| Jan. 9, 1996 | [JP] | Japan | 8-001573 |
| Nov. 25, 1996 | [JP] | Japan | 8-313475 |
| Nov. 28, 1996 | [JP] | Japan | 8-317910 |

[51] Int. Cl.$^6$ .................... A61K 31/70; C08B 37/10
[52] U.S. Cl. ................ 514/56; 514/54; 536/21; 536/54; 536/55; 536/55.1; 536/55.2
[58] Field of Search .............. 536/54, 55.1, 55.2, 536/55, 21; 514/54, 56

[56] References Cited

U.S. PATENT DOCUMENTS

4,273,873  6/1981  Takagi et al. ..................... 435/180

OTHER PUBLICATIONS

Polymeric Phosphonium Salts as a Novel Class of Cationic Biocides; Akihiko Kanazawa, Tomiki Ikeda, and Takeshi Endo; Journal of Polymer Science: Part A: Polymer chemistry, vol. 32, 1997–2001 (1994).
Polymeric Phosphonium Salts as a Novel Class of Cationic Biocides; Akihiko Kanazawa, Tomiki Ikeda, and Takeshi Endo; Journal of Applied Polymer Science, vol. 53, 1245–1249 (1994).
Synthesis and Antimicrobial Activity of Dimethyl–and Trimethyl–Substituted Phosphonium Salts with Alkyl Chains of Various Lengths; Akihiko Kanazawa, Tomiki Ikeda and Takeshi Endo; Antimicrobial Agents and Chemotherapy, May 1994, 945–952.
Polymeric Phosphonium Salts as a Novel Class of Cationic Biocides: Akihiko Kanazawa, Tomiki Ikeda, and Takeshi Endo; Journal of Polymer Science: Part A: Polymer Chemistry, vol. 31, 3031–3038 (1993).
Polymeric Phosphonium Salts as a Novel Class of Cationic Biocides; Akihiko Kanazawa, Tomiki Ikeda, and Takeshi Endo; Journal of Polymer Science: Part A: Polymer Chemistry, vol. 31, 3003–3011 (1993).
Polymeric Phosphonium Salts as a novel Class of Cationic Biocides; Akihiko Kanazawa, Tomiki Ikeda, and Takeshi Endo; Journal of Polymer Science: Part A: Polymer Chemistry, vol. 31, 1467–1472 (1993).
Poilymeric Phosphonium Salts as a Novel Class of Cationic Biocides; Akihiko Kanazawa, Tomiki Ideka, and Takeshi Endo; Journal of Polymer Science: Part A: Polymer Chemistry, vol. 31, 1441–1447 (1993).
Novel Polycationic Biocides: Synthesis and Antibacterial Activity of Polymeric Phosphonium Salts; Journal of Polymer Science: Part A: Polymer Chemistry, vol. 31, 335–343 (1993).

*Primary Examiner*—Elli Peselev
*Attorney, Agent, or Firm*—Leydig, Voit & Mayer, Ltd.

[57] ABSTRACT

The present invention relates to an organic solvent-soluble mucopolysaccharide consisting of an ionic complex of at least one mucopolysaccharide (preferably heparin or heparin derivative) and a quaternary phosphonium, an antibacterial antithrombogenic composition comprising said organic solvent-soluble mucopolysaccharide and an organic polymer material, an antibacterial antithrombogenic composition comprising said organic solvent-soluble mucopolysaccharide and an antibacterial agent (preferably inorganic antibacterial agent such as silver zeolite), and to a medical material comprising said organic solvent-soluble mucopolysaccharide. The organic solvent-soluble mucopolysaccharide, and the antibacterial antithrombogenic composition and medical material containing the same, of the present invention, can easily impart antithrombogenicity and antibacterial property to a polymer to be a base material, which properties being maintained not only immediately after preparation of the material but also after long-term elution. Thus, the organic solvent-soluble mucopolysaccharide and antibacterial antithrombogenic material of the present invention show superior applicability as a material to impart antithrombogenicity and antibacterial ability to medical materials.

22 Claims, No Drawings

5,783,570

1

ORGANIC SOLVENT-SOLUBLE MUCOPOLYSACCHARIDE, ANTIBACTERIAL ANTITHROMBOGENIC COMPOSITION AND MEDICAL MATERIAL

FIELD OF THE INVENTION

The present invention relates to an organic solvent-soluble mucopolysaccharide consisting of an ionic complex of a mucopolysaccharide and a quaternary phosphonium, an antibacterial antithrombogenic composition comprising said organic solvent-soluble mucopolysaccharide and an organic polymer material, an antibacterial antithrombogenic composition comprising said organic solvent-soluble mucopolysaccharide and an antibacterial agent, and to a medical material comprising said organic solvent-soluble mucopolysaccharide.

BACKGROUND OF THE INVENTION

Artificial materials superior in processability, elasticity and flexibility have been widely used as medical materials in recent years. It is expected that they will be increasingly used in a wider area as artificial organs such as artificial kidney, artificial lung, extracorporeal circulation devices and artificial blood vessels, as well as disposable products such as syringes, blood bags, cardiac catheters and the like. These medical materials are required to have, in addition to sufficient mechanical strength and durability, biological safety which particularly means the absence of blood coagulation upon contact with blood, i.e., antithrombogenicity.

Conventionally employed methods for imparting antithrombogenicity to medical materials are generally classified into three groups of (1) immobilizing a mucopolysaccharide (e.g., heparin) or a plasminogen activator (e.g., urokinase) on the surface of a material, (2) modifying the surface of a material so that it carries negative charge or hydrophilicity, and (3) inactivating the surface of a material. Of these, the method of (1) (hereinafter to be referred to briefly as surface heparin method) is further subdivided into the methods of (A) blending of a polymer and an organic solvent-soluble heparin, (B) coating of the material surface with an organic solvent-soluble heparin, (C) ionical bonding of heparin to a cationic group in the material, and (D) covalent bonding of a material and heparin.

Of the above methods, the methods (2) and (3) are capable of affording a stable antithrombogenicity during a long-term contact with body fluids, since protein adsorbs onto the surface of a material to form a biomembrane-like surface. At the initial stage when the material has been introduced into the body (blood contact site) and when various coagulation factors etc. in the body have been activated, however, it is difficult to achieve sufficient antithrombogenicity without an anticoagulant therapy such as heparin administration.

In contrast, the method (1) exhibits, by the action of heparin and urokinase on the surface, an antithrombogenicity or lytic activity on formed thrombus at the early stage of introduction of a medical material, albeit associated with a propensity toward a decreased ability in a long-term use. According to the methods (A), (B) and (C), the long-term use under physiological conditions generally tends to result in easy release of heparins, which in turn gives rise to insufficient property of a medical material to be used after being fixed in the body. The material obtained by the method (D) is beneficial in that heparin is not released easily due to a covalent bond of heparin, whereas conventional bonding method often alters conformation of D-glucosamine and D-glucuronic acid, which are the heparin constituent elements, thereby reducing the anticoagulant effects.

2

Moreover, the methods (C) and (D) require selection of a material containing a functional group usable for the immobilization of heparin or new introduction of the functional group, which then narrows the range from which the material is selected or lowers mechanical strength of the material due to the introduction of a functional group. In addition, the complicated manipulation may increase the number of steps necessary for preparing a medical material.

In consideration of the easiness of imparting antithrombogenicity to the material and the range of selection of adaptable materials, (A) blending of a polymer and an organic solvent-soluble heparin or (B) coating of the material surface with an organic solvent-soluble heparin are most superior methods. The fatal defect of these methods is, as mentioned earlier, easy release of heparin by a long-term use under physiological conditions. Conversely stated, by overcoming this defect, an easy and simple method for imparting an antithrombogenic property, which method having a wide applicability, can be provided.

As a means for overcoming this problem, Japanese Patent Unexamined Publication No. 270823/1990 discloses a method which is characterized by formation of a complex of a natural mucopolysaccharide and a natural or synthetic lipid, and exemplified by a technique including coating the surface of the material with a complex of heparin and biological phospholipid.

However, this method is only useful in that adverse influence on the body is less, since the cationic material (agent for solubilization in organic solvent), which is eluted together during heparin elution, is a natural or synthetic lipid. That is, it is difficult to say that this method has solved the problem of decreased anticoagulant activity due to the elution of heparin in a long-term use.

The medical device which indwells in the body for a long time, such as an intravenous hyperalimentation (hereinafter to be abbreviated as IVH) catheter, is subject to possible infection from living body-material interface. Bacteria grow in the thrombus formed as a result of the contact of blood and material, and the bacterial cells enter the body to cause infection. Thus, the material to be used for such medical device should have both antithrombogenicity and antibacterial activity at the same time. Although an antibacterial antithrombogenic material has been strongly demanded, there has scarcely documented a material applicable to this field.

On the other hand, various techniques have been reported with respect to antibacterial materials. An antibacterial material containing ammonium salt as an antibacterial agent is disclosed in, for example, Japanese Patent Examined Publication Nos. 25301/1992 and 64143/1991; an antibacterial material containing biguanide is disclosed in, for example, Japanese Patent Examined Publication Nos. 80225/1993, 61261/1990 and 10341/1991; and an antibacterial material containing acridine compound is disclosed in, for example, Japanese Patent Examined Publication No. 76343/1991 and others. In addition, Japanese Patent Unexamined Publication Nos. 82511/1995, 53316/1995, 266912/1992 and 310820/1993 disclose an antibacterial material containing a phosphonium salt. Japanese Patent Examined Publication No. 55892/1994 disclose an antibacterial material containing silver protein as an antibacterial active ingredient.

In these techniques, the antibacterial activity is exhibited by only one antibacterial material, and sufficient antibacterial activity against numerous strains cannot be exhibited. In particular, organic antibacterial agents containing ammonium or phosphonium as an active ingredient often show insufficient effects against Gram-negative bacteria. These materials are not adapted to avoid thrombogenesis, and cannot be used as an antibacterial antithrombogenic material applicable to a medical device for long-term indwelling and the like.

SUMMARY OF THE INVENTION

The present invention aims at solving the above-mentioned problems of the prior art technique and providing an antibacterial antithrombogenic material capable of exhibiting superior antibacterial activity and an antithrombogenicity over an extended period of time, which can be used with ease for a wide range of applications.

The present invention also aims at providing an antibacterial antithrombogenic material capable of exhibiting an antithrombogenic property over an extended period of time, and having a wide antibacterial spectrum and superior antibacterial activity.

The present invention provides the following (1)–(22).

(1) Liposoluble mucopolysaccharides consisting of an ionic complex of at least one mucopolysaccharide and a quaternary phosphonium.

(2) The organic solvent-soluble mucopolysaccharides of the above (1), comprising at least one member selected from heparin and heparin derivatives as the mucopolysaccharide.

(3) The organic solvent-soluble mucopolysaccharides of the above (1) or (2), wherein the quaternary phosphonium has the formula (I)

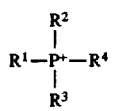

wherein $R^1$, $R^2$ and $R^3$ are the same or different and each is alkyl having 1 to 12 carbon atoms, aryl having 6 to 12 carbon atoms or aralkyl having 7 to 20 carbon atoms, and $R^4$ is alkyl having 1 to 25 carbon atoms.

(4) Antibacterial antithrombogenic compositions comprising the organic solvent-soluble mucopolysaccharide of any one of the above (1)–(3) and an organic polymer material.

(5) The compositions of the above (4), wherein the organic polymer material is selected from the group of poly(vinyl halide), poly(vinylidene halide), polyurethane, polyurethaneurea, polyester and polyamide.

(6) Antibacterial antithrombogenic compositions comprising the organic solvent-soluble mucopolysaccharide of any one of the above (1)–(3), an organic polymer material and an antibacterial agent.

(7) The compositions of the above (6) wherein the organic polymer material is selected from poly(vinyl halide), poly(vinylidene halide), polyurethane, polyurethaneurea, polyester and polyamide.

(8) The compositions of the above (6) wherein the antibacterial agent is an inorganic antibacterial agent.

(9) The compositions of the above (8) wherein the inorganic antibacterial agent is at least one member selected from silver zeolite, silver zirconium phosphate complex, silver ceramics, silver silica and antibacterial glass.

(10) The compositions of the above (8) which comprises 0.1–50 parts by weight of the organic solvent-soluble mucopolysaccharide and 0.1–50 parts by weight of the inorganic antibacterial agent, both relative to 100 parts by weight of the organic polymer material.

(11) Antibacterial antithrombogenic compositions comprising the organic solvent-soluble mucopolysaccharide of any one of the above (1)–(3) and an antibacterial agent.

(12) The compositions of the above (11) wherein the antibacterial agent is an inorganic antibacterial agent.

(13) The compositions of the above (12) wherein the inorganic antibacterial agent is at least one member selected from silver zeolite, silver zirconium phosphate complex, silver ceramics, silver silica and antibacterial glass.

(14) Biomedical materials comprising the organic solvent-soluble mucopolysaccharide of any one of the above (1)–(3).

(15) Biomedical materials comprising the organic solvent-soluble mucopolysaccharide of any one of the above (1)–(3) and an organic polymer material.

(16) Biomedical materials comprising the organic solvent-soluble mucopolysaccharide of any one of the above (1)–(3), an organic polymer material and an antibacterial agent.

(17) Methods for imparting antibacterial property and antithrombogenicity to a medical material, which comprises admixing the organic solvent-soluble mucopolysaccharide of any one of the above (1)–(3) with the medical material.

(18) Methods for imparting antibacterial property and antithrombogenicity to a medical material, which comprises coating the medical material with the organic solvent-soluble mucopolysaccharide of any one of the above (1)–(3).

(19) Methods for imparting antibacterial property and antithrombogenicity to a medical material, which comprises admixing an antibacterial antithrombogenic composition comprising the organic solvent-soluble mucopolysaccharide of any one of the above (1)–(3) and an organic polymer material with the medical material.

(20) Methods for imparting antibacterial property and antithrombogenicity to a medical material, which comprises coating the medical material with an antibacterial antithrombogenic composition comprising the organic solvent-soluble mucopolysaccharide of any one of the above (1)–(3) and an organic polymer material.

(21) Methods for imparting antibacterial property and antithrombogenicity to a medical material, which comprises admixing an antibacterial antithrombogenic composition comprising the organic solvent-soluble mucopolysaccharide of any one of the above (1)–(3), an organic polymer material and an antibacterial agent with the medical material.

(22) Methods for imparting antibacterial property and antithrombogenicity to a medical material, which comprises coating the medical material with an antibacterial antithrombogenic composition comprising the organic solvent-soluble mucopolysaccharide of any one of the above (1)–(3), an organic polymer material and an antibacterial agent.

DETAILED DESCRIPTION OF THE INVENTION

The organic solvent-soluble mucopolysaccharide of the present invention consists of an ionic complex of at least one mucopolysaccharide and a quaternary phosphonium (hereinafter to be referred to as an organic solvent-soluble mucopolysaccharide).

The quaternary phosphonium which is an essential component of the organic solvent-soluble mucopolysaccharide of the present invention has the above-mentioned formula (I). The quaternary phosphonium may be a combination of plural compounds or otherwise. Of the four hydrocarbon chains which bind to the phosphorus atom of quaternary phosphonium, $R^4$ is an alkyl having 1 to 25, preferably 3 to 20, and more preferably alkyl having 6 to 20 carbon atoms. $R^1$, $R^2$ and $R^3$ are each an alkyl having 1 to 12, preferably 1 to 8 carbon atoms, or an aryl having 6 to 12, preferably 6 to 10, carbon atoms, or an aralkyl having 7 to 20, preferably 7 to 12, carbon atoms.

Specifically preferable examples of quaternary phosphonium include tributyldecylphosphonium, tributyllaurylphosphonium, tributylmyristylphosphonium, tributylcetylphosphonium, tributylstearylphosphonium, triphenyldecylphosphonium, triphenyllaurylphosphonium, triphenylmyristylphosphonium, triphenylcetylphosphonium, triphenylstearylphosphonium, benzyldimethyllayrylphosphonium, benzyldimethyldecylphosphonium, benzyldimethylmyristylphosphonium, benzyldimethylcetylphosphonium, benzyldimethylstearylphosphonium and the like. The quaternary phosphonium is not limited to these as long as it is a compound having the structure shown by the formula (I).

The organic solvent-soluble mucopolysaccharide of the present invention essentially contains a mucopolysaccharide. Examples of the mucopolysaccharides include heparin, derivatives of heparin such as alkali metal salts of heparin (e.g., sodium salt of heparin and potassium salt of heparin) and low molecular weight heparin, chondroitin sulfate, hyaluronic acid, dermatan sulfate, keratan sulfate and the like, with preference given to heparin and heparin derivatives, and more preference given to heparin.

A method for obtaining an organic solvent-soluble mucopolysaccharide consisting of an ionic complex of a mucopolysaccharide and a quaternary phosphonium is not particularly limited. For example, a method is exemplified wherein an aqueous solution or an aqueous dispersion of a mucopolysaccharide and an aqueous solution or an aqueous dispersion of a quaternary phosphonium salt are mixed and the resulting precipitate is recovered and lyophilized. Instead of water to be used here, a weak acidic buffer may be used. The solute to be used with the buffer preferably include, for example, 2-(N-morpholino)ethanesulfonic acid, piperazine-1,4-bis(2-ethanesulfonic acid), N-(2-acetamido)-2-aminoethanesulfonic acid, N,N-bis(2-hydroxyethyl)-2-aminoethanesulfonic acid, 3-(N-morpholino)propanesulfonic acid, 3-(N-morpholino)-2-hydroxypropanesulfonic acid, or 2-[4-(2-hydroxyethyl)-1-piperazinyl]ethanesulfonic acid, which is particularly preferably 2-(N-morpholino)ethanesulfonic acid (hereinafter to be abbreviated as MES), piperazine-1,4-bis(2-ethanesulfonic acid) (hereinafter to be abbreviated as PIPES) and 3-(N-morpholino)propanesulfonic acid (hereinafter to be abbreviated as MOPS).

When forming an ionic complex, the mucopolysaccharide and quaternary phosphonium are preferably mixed in a proportion as expressed by a molar ratio of the acid group of mucopolysaccharide to quaternary phosphonium salt of 1:0.3–1:3 and more preferably 1:0.5–1:2.

The antibacterial antithrombogenic composition and medical material of the present invention may contain, besides the organic solvent-soluble mucopolysaccharide, an antibacterial agent. The antibacterial agent is preferably an inorganic antibacterial agent. Examples of the inorganic antibacterial agent include antibacterial agents containing metals such as silver, copper, zinc and the like as an active ingredient, antibacterial glass and the like. The antibacterial agent containing silver as an active ingredient is exemplified by silver zeolite, silver zirconium phosphate complex, silver ceramics, silver silica and the like. In addition, a metal-organic compound complex such as silver protein and sulfadiazine silver can be used in the present invention as an inorganic antibacterial agent. Of these inorganic antibacterial agents, silver antibacterial agent and antibacterial glass are preferably used in the present invention. More preferred is silver zeolite.

The weight ratio of the organic solvent-soluble mucopolysaccharide to the antibacterial agent is preferably 40:1–1:4, more preferably 20:1–1:1.

In the present invention, superior antibacterial activity and wide antibacterial spectrum can be introduced into materials as a result of a synergistic effect of the added inorganic antibacterial agent and a quaternary phosphonium which functions as an agent for solubilization in organic solvent.

The antibacterial antithrombogenic composition and the medical material of the present invention can be those which contain at least an organic solvent-soluble mucopolysaccharide and an organic polymer material. The organic polymer material to be used for the antibacterial antithrombogenic composition and the medical material of the present invention is specifically exemplified by poly(vinyl halide), poly(vinylidene halide), polyurethane, polyurethaneurea, polyester, polyamide, polypropylene, polyethylene and the like, which have been conventionally used, and the materials which will be used in the future. Of these, poly(vinyl halide), poly(vinylidene halide), polyurethane, polyurethaneurea, polyester and polyamide are preferably used, with more preference given to poly(vinyl halide), poly(vinylidene halide), polyurethane and polyurethaneurea.

Generally, poly(vinyl chloride) and poly(vinylidene chloride) conventionally contain aromatic carboxylate or aliphatic carboxylate as a plasticizer. With regard to poly(vinyl chloride), dioctyl phthalate (hereinafter to be abbreviated as DOP) is typically used. In the present invention, such plasticizer can be added to the organic polymer material. In view of the mechanical properties such as processability, elasticity and flexibility that the medical material is requested to have, a plasticizer is desirably added. According to the inventors' studies, addition of a plasticizer often resulted in easier exhibition of antithrombogenicity and antibacterial activity. Although the detail of the mechanism has not been elucidated, the coexistence of a plasticizer appears to improve mobility of the organic solvent-soluble mucopolysaccharide in a polymer, and the organic solvent-soluble mucopolysaccharide exudes into the material-biological component interface while taking a conformation which makes active exertion of the activity easier. While the amount of the plasticizer to be added is not particularly limited, it is 5–100 parts by weight, preferably 10–80 parts by weight, relative to 100 parts by weight of the polymer. According to the present invention, the organic solvent-soluble mucopolysaccharide is introduced into the organic polymer material by adding same in a proportion of 0.1–100 parts by weight, preferably 0.1–50 parts by weight, particularly preferably 1–50 parts by weight, all relative to 100 parts by weight of the organic polymer material (hereinafter when one part by weight of an additive is added to 100 parts by weight of the base material, the amount of the additive is indicated as 1 phr).

The antibacterial antithrombogenic composition and medical material of the present invention can be those which contain at least an organic solvent-soluble mucopolysaccharide, an antibacterial agent and an organic polymer material. As the antibacterial agent, the inorganic antibacterial agent as mentioned earlier is preferable. By the introduction of an organic solvent-soluble mucopolysaccharide and an antibacterial agent into an organic polymer material, the surface of the polymer material is inactivated, and simultaneously, the organic solvent-soluble mucopolysaccharide and a part of the antibacterial agent are released from the organic polymer material, thereby enabling exertion of antithrombogenicity and antibacterial activity. In the composition and medical material of the present invention which show antithrombogenicity and antibacterial activity, the release of the organic solvent-soluble mucopolysaccharide and antibacterial agent is suppressed even upon contact with biological components, as a result of the affinity for the organic polymer material and the organic solvent-soluble mucopolysaccharide and antibacterial agent, and extremely superior antithrombogenicity and antibacterial activity can be maintained after a long-term contact with the biological components.

In the present invention, the amounts of the organic solvent-soluble mucopolysaccharide and the inorganic antibacterial agent when they are introduced into an organic polymer material are preferably about 0.1 phr–100 phr, more preferably 0.1 phr–50 phr, particularly preferably 1 phr–50 phr of organic solvent-soluble mucopolysaccharide relative to the organic polymer material. The inorganic antibacterial agent is preferably added in an amount of about 0.1 phr–50 phr, more preferably about 1 phr–30 phr, relative to the organic polymer material, and the weight ratio of the organic solvent-soluble mucopolysaccharide and inorganic antibacterial agent to be added is preferably 40:1–1:4, more preferably 20:1–1:1.

The antibacterial antithrombogenic composition and medical material of the present invention can be further introduced into a different structure to be the base material. The material of the structure is not particularly limited and is exemplified by polyether-urethane, polyurethane, polyurethaneurea, poly(vinyl chloride), poly(vinylidene chloride), polyester, polypropylene, polyethylene, polycarbonate and the like, which have been conventionally used, and the materials which will be used in the future. It may be introduced into blood dialysis membranes, plasma separation membranes, blood treating agents such as adsorbents, and the like which are made from an existing or novel material potentially used in the future, so as to impart antithrombogenicity.

The method for introduction into the base material is not particularly limited, and conventional blending method and coating method can be employed. The coating method is subject to no particular limitation and coating method, spray method, dip method and the like may be employed. Of these methods, a method which does not give thermal hysteresis to the physiologically active substance mucopolysaccharides is preferably used.

The medical material of the present invention can be that comprising a base material having its surface coated with an organic solvent-soluble mucopolysaccharide. Also, the medical material of the present invention can be that comprising a base material having its surface coated with an antibacterial antithrombogenic composition comprising an organic solvent-soluble mucopolysaccharide and an organic polymer material. Alternatively, the medical material of the present invention can be that comprising a base material having its surface coated with an antibacterial antithrombogenic composition comprising an organic solvent-soluble mucopolysaccharide and an antibacterial agent. In addition, the medical material of the present invention can be that comprising a base material having its surface coated with an antibacterial antithrombogenic composition comprising an organic solvent-soluble mucopolysaccharide, an organic polymer material and an antibacterial agent. The antibacterial agent to be used is preferably an inorganic antibacterial agent as described earlier. Examples of the organic polymer material include poly(vinyl halide), poly(vinylidene halide), polyurethane, polyurethaneurea, polyester, polyamide, polypropylene, polyethylene, and the like, with preference given to poly(vinyl halide), poly(vinylidene halide), polyurethane, polyurethaneurea, polyester and polyamide. The material of the base material may be a conventional one widely used heretofore such as organic polymers, which is exemplified by polyether-urethane, polyurethane, polyurethaneurea, poly(vinyl chloride), poly(vinylidene chloride), polyester, polypropylene, polyethylene, polycarbonate and the like.

Although the detail of the mechanism has not been elucidated, an organic solvent-soluble mucopolysaccharide, and the antibacterial antithrombogenic composition and medical material of the present invention containing the same can maintain fine anti-coagulation property, i.e. antithrombogenicity, during, not to mention the early stages of contact with the biological components, but a long-term contact therewith. In addition, superior antibacterial property can be imparted by the effect of a quaternary phosphonium or as a result of a synergistic effect of a quaternary phosphonium and an antibacterial agent (particularly quaternary phosphonium and inorganic antibacterial agent).

Making the most of such advantages, the organic solvent-soluble mucopolysaccharide, an antibacterial antithrombogenic composition and a medical material both containing the same of the present invention can be widely used for making materials for various medical instruments and mechanical devices antithrombogenic. To be specific, they can be used for blood dialysis membranes, plasma separation membranes and coating agents thereof, coating agents for adsorption of waste substances in blood. In addition, they can be used for a wide variety of uses such as membrane (partition wall between blood and oxygen) for artificial lung, sheet material of sheet lung in artificial heart-lung, artery balloon, blood bag, catheter, cannula, shunt, blood circuit and the like. The property of the organic solvent-soluble mucopolysaccharide and antibacterial antithrombogenic material of the present invention that they both have antibacterial activity can be utilized for the application to IVH associated with possible infection from body-material interface. For example, they can be used for medical devices such as IVH catheters.

The present invention is hereinafter explained by referring to Examples.

EXAMPLE 1

Heparin sodium salt (10.00 g) was dissolved in ion-exchange water to a total amount of 100 ml. Tri-n-butylcetylphosphonium chloride (hereinafter to be abbreviated as TBCP-Cl, 19.07 g) was dissolved in ion-exchange water to a total amount of 191 ml. The both solutions were mixed under ice-cooling, and stood for 15 hr at 4° C. to give a suspension. This suspension was centrifuged at 3300 rpm to recover the precipitate. Three repeats of washing by adding distilled water to suspend the precipitates and centrifugation, and subsequent drying of the precipitates gave a complex of TBCP-Cl and heparin (hereinafter to be abbreviated as TBCP-Hep). This TBCP-Hep was soluble in organic solvents such as benzene, DMF, THF, chloroform and the like.

Commercially available polyurethane (Tecoflex, trademark, hereinafter to be abbreviated as PU) was dissolved in THF to give a 5% solution. This PU solution (20 g) was uniformly placed on a 12 cm×12 cm glass plate which was kept even, and dried at 40° C. in a nitrogen stream for 8 hr and then at 40° C. under reduced pressure to give about a 60 μm thick film.

The TBCP-Hep obtained above was dissolved in THF to give a 0.1% solution. This solution (3.00 g) was uniformly placed on the PU film obtained above, dried at 40° C. in a nitrogen stream for 8 hr and at 40° C. for 15 hr under reduced pressure to give a TBCP-Hep coating PU film 1.

Plasma relative coagulation time on the film 1 obtained above was evaluated by the following method.

The film 1 was cut into a 3 cm diameter disc and pasted at the middle of a 10 cm diameter watch glass. On this film was placed citrated rabbit (Japanese White Rabbit) plasma (200 μl), and an aqueous calcium chloride solution (200 μl, 0.025 mol/l) was added, which was then gently shaken while being floated in an incubator at 37° C., so that the solutions on the watch glass could be admixed. The lapse of time from the addition of the aqueous calcium chloride solution to the coagulation of the plasma (the point when plasma became still) was measured. The measure was divided by the time necessary for plasma coagulation when the same procedure was performed on a glass plate, and used as relative coagulation time. When the plasma did not coagulate, after 12 times longer time than the coagulation time on the glass, the evaluation was stopped and the relative coagulation time was indicated as >12. The results are shown in Table 1 to be given later.

The TBCP-Hep (material 1) was dissolved in THF to give a 0.1% solution. Glass beads (40–60 mesh) were immersed in this solution for 30 min, and collected by filtration through a glass filter. After drying at 40° C. under a nitrogen stream for 8 hr, the beads were dried at 40° C. for 15 hr under reduced pressure to coat the material 1 on the glass beads surface. These coated beads (100 mg) were immersed in a 2-fold diluted suspension (1 ml) of human serum with PBS, and incubated at 37° C. for 30 min with gentle shaking. Using this solution as a sample, 50% hemolytic unit of complement (CH50) was determined by the Mayer method (Mayer, M. M., "Complement and Complement fixation", Experimental Immunochemistry 2nd Ed. pp. 133–240, C. C. Thomas Publisher, 1961). The results are shown in Table 1 in percentage relative to the hemolytic unit of complement of 1 ml of the above-mentioned dilute serum without beads.

The antibacterial activity of film 1 was evaluated by the following method wherein a series of steps were conducted under germ-free environment.

Using a broth (diluted 50-fold with sterilized physiological saline), a suspension of *Pseudomonas aeruginosa* was prepared so that the number of organisms would be about $1 \times 10^7$/ml (hereinafter this organism suspension is called a stock suspension). The cells in this stock suspension were counted as follows. The stock suspension was diluted $10^4$-fold and 100 μl thereof was plated on a regular agar plate, and the colonies of *Pseudomonas aeruginosa* formed in 24 hr were counted. The number of colonies being N, the number C of organisms per milliliter of the stock suspension is expressed by the formula $$C = 10^4 \times N/0.1 = 10^5 \times N \text{ [cells/ml]}$$

This stock suspension (100 μl) was diluted with a broth (diluted 40-fold with sterilized physiological saline) to a total amount of 40 ml (hereinafter this solution is called immersing suspension). A 5 cm×5 cm EOG sterilized film 1 was immersed in the immersing suspension and incubated at 37° C. for 24 hr. After incubation, the immersing suspension was diluted $10^4$-fold in a 10-fold series with sterilized physiological saline (hereinafter to be referred to briefly as $10^n$-fold diluted suspension). The immersing suspension and diluted suspension (100 μl each) were plated on a regular agar medium, and the colonies of *Pseudomonas aeruginosa* formed on the medium in 24 hr were counted with respect to 30–300 plates. The number of colonies from the diluted suspension being $N_n$, the number of cells $N_a$ after contact with 25 cm² film 1 is expressed by the following formula $$N_a = 40 \times 10^n \times N_n / 0.1$$

Since the number of organisms per milliliter of the stock suspension before contact with film 1 was C as mentioned above, and the amount thereof used was 100 μl, the number of cells $N_b$ before contact with film 1 was $$N_b = 10^5 \times N$$

Changes in the cell number from Nb to Na by the contact with the 25 cm² size film in 40 ml of the immersing suspension are shown in Table 1. A decrease in the number of cells due to the contact means that the antibacterial activity of the film was exerted.

A 0.1% solution of TBCP-Hep in THF was prepared and a porous polypropylene hollow fiber for artificial lung was immersed therein and pulled out, which was followed by 12 hours' drying at 40° C. to coat the hollow fiber. Using this hollow fiber, in vivo antithrombogenicity was evaluated. The test method was as follows.

The femoral vein of a rabbit (Japanese White Rabbits, male, 2.5–3.0 kg) was detached under pentobarbital anesthesia. The peripheral end thereof was ligated with a yarn, and clamped with a hemostat at a site 2–3 cm from the yarn. The central side of the ligated section was cut with a scalpel to ¼–⅓ of the diameter of the blood vessel. A sample hollow fiber was inserted 10 cm therefrom toward the central side. At 1 cm from the insertion site, the end portion of the hollow fiber extending from the blood vessel was sewn to prevent the hollow fiber from being carried away. The incised section was sutured and an antibiotic was administered. The rabbits were bred for 2 weeks until the sample was taken out. Two weeks later, the rabbits underwent median incision under heparinized pentobarbital anesthesia, and a suitable tube was inserted into the abdominal aorta for exsanguination to sacrifice the rabbits. Then, the blood vessel into which the hollow fiber had been inserted was sectioned. The blood vessel was incised and the hollow fiber and the inside of the blood vessel were photodocumented, and visually observed for 5 rank evaluation. The results are shown in Table 1.

The film 1 was immersed in PBS, and eluted in a shake incubator at 37° C. for 2 weeks. PBS was changed every day. Hereinafter the film after elution is called film 1'. In the same manner as with film 1, plasma relative coagulation time and antibacterial activity were evaluated with respect to film 1'. The results are shown in Table 1.

TABLE 1

| | | Relative coagulation time (glass = 1.00) | Hemolytic unit of Complement | Antibacterial activity (X10⁶ cells/ 40 ml) | in vivo antithrombogenicity |
|---|---|---|---|---|---|
| Example 1 | 1 | >12 | 98% | 7.100 → N.D. | b |
| | 1' | 9.9 | — | 7.100 → 0.010 | — |
| Example 2 | 2 | >12 | 98% | 7.100 → N.D. | b |
| | 2' | 9.8 | — | 7.100 → N.D. | — |
| Example 3 | 3 | >12 | 97% | 7.100 → N.D. | a |
| | 3' | >12 | — | 7.100 → N.D. | — |

TABLE 1-continued

|  | | Relative coagulation time (glass = 1.00) | Hemolytic unit of Complement | Antibacterial activity (X10⁶ cells/ 40 ml) | in vivo anti-thrombo-genicity |
|---|---|---|---|---|---|
| Example 4 | 4 | >12 | 99% | 7.100 → N.D. | a |
|  | 4' | >12 | — | 7.100 → N.D. | — |
| Example 5 | 5 | >12 | 98% | 7.100 → N.D. | a |
|  | 5' | >12 | — | 7.100 → N.D. | — |
| Example 6 | 6 | >12 | 98% | 7.100 → N.D. | a |
|  | 6' | >12 | — | 7.100 → N.D. | — |
| Example 7 | 7 | >12 | 98% | 7.100 → N.D. | a |
|  | 7' | >12 | — | 7.100 → N.D. | — |
| Example 8 | 8 | >12 | 97% | 7.100 → N.D. | a |
|  | 8' | >12 | — | 7.100 → N.D. | — |
| Example 9 | 9 | >12 | 98% | 7.100 → N.D. | a |
|  | 9' | >12 | — | 7.100 → N.D. | — |
| Example 10 | 10 | >10 | 98% | 7.100 → N.D. | a |
|  | 10' | >12 | — | 7.100 → N.D. | — |
| Example 11 | 11 | >12 | 98% | 7.100 → N.D. | a |
|  | 11' | >12 | — | 7.100 → N.D. | — |
| Example 12 | 12 | >12 | 98% | 7.100 → N.D. | a |
|  | 12' | >12 | — | 7.100 → N.D. | — |
| Example 13 | 13 | >12 | 98% | 7.100 → N.D. | a |
|  | 13' | >12 | — | 7.100 → N.D. | — |
| Example 14 | 11" | 9.0 | — | 7.100 → 0.010 | — |
|  | 12" | 9.4 | — | 7.100 → 0.005 | — |
|  | 13" | 9.8 | — | 7.100 → N.D. | — |
| Compar. Ex. 1 | 15 | 10.6 | 84% | 7.100 → N.D. | b |
|  | 15' | 4.3 | — | 7.100 → 0.510 | — |
| Compar. Ex. 2 | 16 | 9.8 | 83% | 7.100 → N.D. | b |
|  | 16' | 3.9 | — | 7.100 → 0.710 | — |
| Compar. Ex. 3 | 17 | 10.9 | 80% | 7.100 → 0.020 | b |
|  | 17' | 5.9 | — | 7.100 → 0.120 | — |
| Compar. Ex. 4 | 18 | 9.7 | 80% | 7.100 → N.D. | b |
|  | 18' | 3.3 | — | 7.100 → 0.090 | — |
| Compar. Ex. 5 | 19 | 3.1 | 75% | 7.100 → 0.230 | c |
|  | 19' | 2.9 | — | 7.100 → 0.440 | — |
| Compar. Ex. 6 | 20 | 2.9 | 69% | 7.100 → N.D. | c |
|  | 20' | 3.2 | — | 7.100 → 0.105 | — |
| Compar. Ex. 7 | 21 | 2.8 | 76% | 7.100 → N.D. | c |
|  | 21' | 3.0 | — | 7.100 → 0.090 | — |
| Compar. Ex. 8 | 22 | 3.0 | 70% | 7.100 → N.D. | c |
|  | 22' | 3.0 | — | 7.100 → 0.110 | — |
| Compar. Ex. 9 | 23 | 2.7 | 68% | 7.100 → N.D. | c |
|  | 23' | 3.2 | — | 7.100 → 1.005 | — |
| Compar. Ex. 10 | 24 | 3.0 | 70% | 7.100 → N.D. | c |
|  | 24' | 2.8 | — | 7.100 → 0.105 | — |
| Compar. Ex. 11 | 25 | 3.1 | — | 7.100 → 7.210 | — |
|  | 25' | 2.9 | — | 7.100 → 7.190 | — |

The 5 rank evaluation of in vivo antithrombogenicity in Table 1 was based on the following criterion.

a: Absence of platelet coagulation, thrombus formation and fibrin formation.
b: Fibrin formation or platelet coagulation was found, but thrombus formation was not observed.
c: Fibrin formation or platelet coagulation was found and thrombus formation was slightly observed.
d: Fibrin formation or platelet coagulation was found and thrombus formation was found to a considerable extent.
e: Fibrin formation or platelet coagulation was found and a large amount of thrombus appeared to have been formed.

EXAMPLE 2

THF was added to TBCP-Hep (200 mg) obtained in Example 1 and commercially available antibacterial agent silver zeolite (20 mg, Zeomic (trademark) manufactured by Sinanen Co., Ltd., hereinafter to be abbreviated as AgZeo) to make the total amount 100 g, whereby a TBCP-Hep, AgZeo/THF suspension was obtained. This suspension (3.00 g) was uniformly placed on a 12 cm×12 cm PU film, and dried at 40° C. for 8 hr under a nitrogen stream, and then at 40° C. for 15 hr under reduced pressure, to give a ca. 60 μm thick film (hereinafter this TBCP-Hep.AgZeo coating PU film is to be referred to briefly as film 2).

In the same manner as in Example 1, the plasma relative coagulation time and antibacterial activity of film 2 were determined. Also, glass beads were coated with TBCP-Hep, AgZeo/THF suspension and in the same manner as in Example 1, hemolytic unit of complement was determined. Further, in the same manner as in Example 1, film 2 was subjected to elution test. The obtained elution film 21 was tested for plasma relative coagulation time and antibacterial activity. The results are shown in Table 1.

EXAMPLE 3

To 1000 g of a 5% PU solution in THF was added 10.0 g of TBCP-Hep obtained in Example 1 to give a homogeneous solution. This TBCP-Hep/PU blend solution (20 g) was uniformly placed on a 12 cm×12 cm glass plate kept even, and dried at 40° C. for 8 hr under a nitrogen stream and then at 40° C. under reduced pressure, to give an about 60 μm thick film (hereinafter this TBCP-Hep/PU blend material is to be referred to briefly as material 3, and the film obtained from material 3 as film 3). The film 3 contained 20 phr of TBCP-Hep. In the same manner as in Example 1 using film 3, plasma relative coagulation time, antibacterial activity and in vivo antithrombogenicity were measured. Also, material 3 was dissolved in THF, and glass beads were coated with this solution. The hemolytic unit of complement was determined in the same manner as in Example 1. In the same manner as in Example 1, film 3 was subjected to an elution test and the obtained elution film 3' was tested for plasma relative coagulation time and antibacterial activity. The results are shown in Table 1.

EXAMPLE 4

Commercially available poly(vinyl chloride) (DOP content 50 phr, hereinafter this poly(vinyl chloride) is to be abbreviated as PVC) was dissolved in THF to give a 5% solution. To 1000 g of this PVC solution was added 10.0 g of TBCP-Hep obtained in Example 1 to give a homogeneous solution. This TBCP-Hep/PVC blend solution (20 g) was uniformly placed on a 12 cm×12 cm glass plate kept even, and dried at 40° C. for 8 hr under a nitrogen stream and then at 40° C. for 15 hr under reduced pressure, to give an about 60 μm thick film (hereinafter this TBCP-Hep/PVC blend material is to be referred to briefly as material 4, and the film obtained from material 4 as film 4). The film 4 contained 20 phr of TBCP-Hep. In the same manner as in Example 1 using film 4, plasma relative coagulation time, antibacterial activity and in vivo antithrombogenicity were determined. Also, material 4 was dissolved in THF, and glass beads were coated with this solution. The hemolytic unit of complement was determined in the same manner as in Example 1. In the same manner as in Example 1, film 4 was subjected to an elution test and the obtained elution film 4' was tested for plasma relative coagulation time and antibacterial activity. The results are shown in Table 1.

EXAMPLE 5

To 1000 g of a 5% PU solution in THF were added 10.0 g of TBCP-Hep obtained in Example 1 and 1.00 g of AgZeo to give a homogeneous suspension. This TBCP-Hep.AgZeo/ PU blend suspension (20 g) was uniformly placed on a 12 cm×12 cm glass plate kept even, and dried at 40° C. for 8 hr under a nitrogen stream and then at 40° C. for 15 hr under reduced pressure to give an about 60 μm thick film (hereinafter this TBCP-Hep,AgZeo/PU blend material is to be referred to briefly as material 5, and the film obtained from material 5 as film 5). The film 5 contained 20 phr of TBCP-Hep and 2 phr of AgZeo. In the same manner as in Example 1 using film 5, plasma relative coagulation time, antibacterial activity and in vivo antithrombogenicity were determined. Also, material 5 was suspended in THF, and glass beads were coated with this suspension. The hemolytic unit of complement was determined in the same manner as in Example 1. In the same manner as in Example 1, film 5 was subjected to an elution test and the obtained elution film 5' was tested for plasma relative coagulation time and antibacterial activity. The results are shown in Table 1.

EXAMPLE 6

In the same manner as in Example 5 except that PU was changed to PVC, a TBCP-Hep,AgZeo/PVC blend material 6 containing 20 phr of TBCP-Hep and 2 phr of AgZeo, and film 6 were obtained. In the same manner as in Example 1 using film 6, plasma relative coagulation time, antibacterial activity and in vivo antithrombogenicity were determined. Also, material 6 was suspended in THF, and glass beads were coated with this suspension. The hemolytic unit of complement was determined in the same manner as in Example 1. In the same manner as in Example 1, film 6 was subjected to an elution test and the obtained elution film 6' was tested for plasma relative coagulation time and antibacterial activity. The results are shown in Table 1.

EXAMPLE 7

Heparin sodium salt (10.00 g) was dissolved in ion-exchange water to make the total amount 100 ml. Tri-n-butyllaurylphosphonium chloride (16.76 g, hereinafter to be abbreviated as TBLP-Cl) was dissolved in ion-exchange water to make the total amount 168 ml. The both solutions were mixed under ice-cooling and stood at 4° C. for 15 hr to give a suspension. This suspension was centrifuged at 3300 rpm to recover precipitates. The precipitates were washed three times by adding distilled water to give a suspension and centrifugation. Then, the precipitates were dried to give a complex of TBLP-Cl and heparin (hereinafter to be abbreviated as TBLP-Hep). This TBLP-Hep was soluble in organic solvents such as benzene, DMF, THF, chloroform and the like.

In the same manner as in Example 3 except that the organic solvent-soluble heparin was changed from TBCP-Hep to TBLP-Hep, a TBCP-Hep/PU blend material 7 and film 7 made from material 7 were obtained. In the same manner as in Example 1 using material 7 and film 7, plasma relative coagulation time, hemolytic unit of complement, antibacterial activity and in vivo antithrombogenicity were determined. In the same manner as in Example 1, film 7 was subjected to an elution test and the obtained elution film 7' was tested for plasma relative coagulation time and antibacterial activity. The results are shown in Table 1.

EXAMPLE 8

In the same manner as in Example 4 except that the organic solvent-soluble heparin was changed from TBCP-Hep to TBLP-Hep, a TBLP-Hep/PVC blend material 8 and film 8 made from material 8 were obtained. In the same manner as in Example 1 using material 8 and film 8, plasma relative coagulation time, hemolytic unit of complement, antibacterial activity and in vivo antithrombogenicity were determined. In the same manner as in Example 1, film 8 was subjected to an elution test and the obtained elution film 8' was tested for plasma relative coagulation time and antibacterial activity. The results are shown in Table 1.

EXAMPLE 9

In the same manner as in Example 5 except that the organic solvent-soluble heparin was changed from TBCP-Hep to TBLP-Hep, a TBLP-Hep,AgZeo/PU blend material 9 and film 9 made from material 9 were obtained. In the same manner as in Example 1 using material 9 and film 9, plasma relative coagulation time, hemolytic unit of complement, antibacterial activity and in vivo antithrombogenicity were determined. In the same manner as in Example 1, film 9 was subjected to an elution test and the obtained elution film 9' was tested for plasma relative coagulation time and antibacterial activity. The results are shown in Table 1.

EXAMPLE 10

In the same manner as in Example 6 except that the organic solvent-soluble heparin was changed from TBCP-Hep to TBLP-Hep, a TBLP-Hep,AgZeo/PVC blend material 10 and film 10 made from material 10 were obtained. In the same manner as in Example 1 using material 10 and film 10, plasma relative coagulation time, hemolytic unit of complement, antibacterial activity and in vivo antithrombogenicity were determined. In the same manner as in Example 1, film 10 was subjected to an elution test and the obtained elution film 10' was tested for plasma relative coagulation time and antibacterial activity. The results are shown in Table 1.

EXAMPLE 11

Heparin sodium salt (10.00 g) was dissolved in ion-exchange water to make the total amount 100 ml. Tri-n-butylmyristylphosphonium chloride (17.91 g, hereinafter to be abbreviated as TBMP-Cl) was dissolved in ion-exchange water to make the total amount 179 ml. The both solutions were mixed under ice-cooling and stood at 4° C. for 15 hr to give a suspension. This suspension was centrifuged at 3300 rpm to recover precipitates. The precipitates were washed three times by adding distilled water to give a suspension and centrifugation. Then, the precipitates were dried to give a complex of TBMP-Cl and heparin (hereinafter to be abbreviated as TBMP-Hep). This TBMP-Hep was soluble in organic solvents such as benzene, DMF, THF, chloroform and the like.

In the same manner as in Example 3 except that the organic solvent-soluble heparin was changed from TBCP-Hep to TBMP-Hep, a TBMP-Hep/PU blend material 11 and film 11 made from material 11 were obtained. In the same manner as in Example 1 using material 11 and film 11, plasma relative coagulation time, hemolytic unit of complement, antibacterial activity and in vivo antithrombogenicity were determined. In the same manner as in Example 1, film 11 was subjected to an elution test and the obtained elution film 11' was tested for plasma relative coagulation time and antibacterial activity. The results are shown in Table 1.

EXAMPLE 12

To 1000 g of a 5% PU solution in THF were added 5.00 g of TBCP-Hep obtained in Example 1 and 5.00 g of TBLP-Hep obtained in Example 7 to give a homogeneous solution. This TBCP-Hep,TBLP-Hep/PU blend solution (20 g) was uniformly placed on a 12 cm×12 cm glass plate kept even, and dried at 40° C. for 8 hr under a nitrogen stream, and then at 40° C. for 15 hr under reduced pressure to give an about 60 μm thick film (hereinafter this TBCP-Hep, TBLP-Hep/PU blend material is to be referred to briefly as material 12, and the film obtained from material 12 as film 12). The film 12 contained 10 phr of TBCP-Hep and 10 phr of TBLP-Hep. In the same manner as in Example 1 using film 12, plasma relative coagulation time, antibacterial activity and in vivo antithrombo-genicity were determined. Also, material 12 was dissolved in THF, and glass beads were coated with this solution. The hemolytic unit of complement was determined by a test similar to that in Example 1. In the same manner as in Example 1, film 12 was subjected to an elution test and the obtained elution film 12' was tested for plasma relative coagulation time and antibacterial activity. The results are shown in Table 1.

EXAMPLE 13

To 1000 g of a 5% PU solution in THF were added 5.00 g of TBCP-Hep obtained in Example 1, 5.00 g of TBLP-Hep obtained in Example 7 and 1.00 g of AgZeo to give a homogeneous suspension. This TBCP-Hep,TBLP-Hep, AgZeo/PU blend suspension (20 g) was uniformly placed on a 12 cm×12 cm glass plate kept even, and dried at 40° C. for 8 hr under a nitrogen stream and then at 40° C. for 15 hr under reduced pressure to give an about 60 μm thick film (hereinafter this TBCP-Hep,TBLP-Hep,AgZeo/PU blend material is to be referred to briefly as material 13, and the film obtained from material 13 as film 13). The film 13 contained 10 phr of TBCP-Hep, 10 phr of TBLP-Hep and 2 phr of AgZeo. In the same manner as in Example 1 using film 13, plasma relative coagulation time, antibacterial activity and in vivo antithrombogenicity were determined. Also, material 13 was suspended in THF, and glass beads were coated with this suspension. The hemolytic unit of complement was determined in the same manner as in Example 1. In the same manner as in Example 1, film 13 was subjected to an elution test and the obtained elution film 13' was tested for plasma relative coagulation time and antibacterial activity. The results are shown in Table 1.

EXAMPLE 14

Film 11, film 12 and film 13 were immersed in citrated bovine plasma, and eluted in a shake incubator at 37° C. for 2 weeks. The citrated bovine plasma was changed every other day. Hereinafter the films after the elution are called film 11", film 12" and film 13", respectively. In the same manner as with film 1, plasma relative coagulation time and antibacterial activity were evaluated with respect to these three kinds of films. The results are shown in Table 1.

Comparative Example 1

Heparin sodium salt (10.00 g) was dissolved in ion-exchange water to make the total amount 100 ml. This solution and a 10% aqueous benzalkonium chloride (hereinafter to be abbreviated as Ben-Cl) solution (142 ml) were mixed under ice-cooling and stood at 4° C. for 15 hr to give a suspension. This suspension was centrifuged at 3300 rpm to recover precipitates. The precipitates were washed three times by adding distilled water and centrifugation. Then, the precipitates were dried to give a complex of Ben-Cl and heparin (hereinafter to be abbreviated as Ben-Hep). This Ben-Hep was soluble in organic solvents such as benzene, DMF, chloroform and the like.

In the same manner as in Example 1 except that the organic solvent-soluble heparin was changed from TBCP-Hep to Ben-Hep, a Ben-Hep coating PU film 15 was obtained. In the same manner as in Example 1 using film 15, plasma relative coagulation time, antibacterial activity and in vivo antithrombogenicity were determined. Also, Ben-Hep was dissolved in THF, and glass beads were coated with this solution. The hemolytic unit of complement was determined in the same manner as in Example 1. In the same manner as in Example 1, film 15 was subjected to an elution test and the obtained elution film 15' was tested for plasma relative coagulation time and antibacterial activity. The results are shown in Table 1.

Comparative Example 2

In the same manner as in Example 2 except that the organic solvent-soluble heparin was changed from TBCP-Hep to Ben-Hep, a Ben-Hep,AgZeo coating PU film 16 was obtained. In the same manner as in Example 1 using film 16, plasma relative coagulation time, antibacterial activity and in vivo antithrombogenicity were determined. Glass beads were coated with a Ben-Hep,AgZeo/THF suspension, and the hemolytic unit of complement was determined in the same manner as in Example 1. In the same manner as in Example 1, film 16 was subjected to an elution test and the obtained elution film 16' was tested for plasma relative coagulation time and antibacterial activity. The results are shown in Table 1.

Comparative Example 3

In the same manner as in Example 3 except that the organic solvent-soluble heparin was changed from TBCP-Hep to Ben-Hep, a Ben-Hep/PU blend material 17 and film 17 made from material 17 were obtained. In the same manner as in Example 1 using the material 17 and film 17, plasma relative coagulation time, hemolytic unit of complement, antibacterial activity and in vivo antithrombogenicity were determined. In the same manner as in Example 1, film 17 was subjected to an elution test and the obtained elution film 17' was tested for plasma relative coagulation time and antibacterial activity. The results are shown in Table 1.

Comparative Example 4

In the same manner as in Example 5 except that the organic solvent-soluble heparin was changed from TBCP-Hep to Ben-Hep, a Ben-Hep,AgZeo/PU blend material 18 and film 18 made from material 18 were obtained. In the same manner as in Example 1 using the material 18 and film 18, plasma relative coagulation time, hemolytic unit of complement, antibacterial activity and in vivo antithrombogenicity were determined. In the same manner as in Example 1, film 18 was subjected to an elution test and the obtained elution film 18' was tested for plasma relative coagulation time and antibacterial activity. The results are shown in Table 1.

Comparative Example 5

Dextran sulfate sodium salt (10.00 g) was dissolved in ion-exchange water to make the total amount 100 ml. TBCP-Cl (29.47 g) was dissolved in ion-exchange water to make the total amount 295 ml. The both solutions were mixed under ice-cooling and stood at 4° C. for 15 hr to give a suspension. This suspension was centrifuged at 3300 rpm to recover precipitates. The precipitates were washed three times by adding distilled water to give a suspension and centrifugation. Then, the precipitates were dried to give a complex of TBCP-Cl and dextran sulfate (hereinafter to be abbreviated as TBCP-Dex). This TBCP-Dex was soluble in organic solvents such as DMF, THF, chloroform and the like.

In the same manner as in Example 3 except that the organic solvent-soluble mucopolysaccharide was changed from TBCP-Hep to TBCP-Dex, a TBCP-Dex/PU blend material 19 and film 19 made from material 19 were obtained. In the same manner as in Example 1 using the material 19 and film 19, plasma relative coagulation time, hemolytic unit of complement, antibacterial activity and in vivo antithrombogenicity were determined. In the same manner as in Example 1, film 19 was subjected to an elution test and the obtained elution film 19' was tested for plasma relative coagulation time and antibacterial activity. The results are shown in Table 1.

Comparative Example 6

In the same manner as in Example 5 except that the organic solvent-soluble mucopolysaccharide was changed from TBCP-Hep to TBCP-Dex, a TBCP-Dex,AgZeo/PU blend material 20 and film 20 made from material 20 were obtained. In the same manner as in Example 1 using the material 20 and film 20, plasma relative coagulation time, hemolytic unit of complement, antibacterial activity and in vivo antithrombogenicity were determined. In the same manner as in Example 1, film 20 was subjected to an elution test and the obtained elution film 20' was tested for plasma relative coagulation time and antibacterial activity. The results are shown in Table 1.

Comparative Example 7

Dextran sulfate sodium salt (10.00 g) was dissolved in ion-exchange water to make the total amount 100 ml. TBLP-Cl (25.90 g) was dissolved in ion-exchange water to make the total amount 259 ml. The both solutions were mixed under ice-cooling and stood at 4° C. for 15 hr to give a suspension. This suspension was centrifuged at 3300 rpm to recover precipitates. The precipitates were washed three times by adding distilled water to give a suspension and centrifugation. Then, the precipitates were dried to give a complex of TBLP-Cl and dextran sulfate (hereinafter to be abbreviated as TBLP-Dex). This TBLP-Dex was soluble in organic solvents such as DMF, THF, chloroform and the like.

In the same manner as in Example 13 except that the organic solvent-soluble mucopolysaccharide TBCP-Hep was changed to TBCP-Dex and the organic solvent-soluble mucopolysaccharide TBLP-Hep was changed to TBLP-Dex, a TBCP-Dex,TBLP-Dex,AgZeo/PU blend material 21 and film 21 made from material 21 were obtained. In the same manner as in Example 1 using the material 21 and film 21, plasma relative coagulation time, hemolytic unit of complement, antibacterial activity and in vivo antithrombogenicity were determined. In the same manner as in Example 1, film 21 was subjected to an elution test and the obtained elution film 21' was tested for plasma relative coagulation time and antibacterial activity. The results are shown in Table 1.

Comparative Example 8

To 1000 g of a 5% PU solution in THF was added 1.00 g of AgZeo to give a homogeneous suspension. This AgZeo/PU blend suspension (20 g) was uniformly placed on a 12 cm×12 cm glass plate kept even, and dried at 40° C. for 8 hr under a nitrogen stream and then at 40° C. for 15 hr under reduced pressure to give an about 60 µm thick film (hereinafter this AgZeo/PU blend material is to be referred to briefly as material 22, and the film obtained from the material 22 as film 22). The film 22 contained 2 phr of AgZeo. In the same manner as in Example 1 using film 22, plasma relative coagulation time, antibacterial activity and in vivo antithrombogenicity were determined. Also, material 22 was suspended in THF, and glass beads were coated with this suspension. The hemolytic unit of complement was determined in the same manner as in Example 1. In the same manner as in Example 1, film 22 was subjected to an elution test and the obtained elution film 22' was tested for plasma relative coagulation time and antibacterial activity. The results are shown in Table 1.

Comparative Example 9

To 1000 g of a 5% PU solution in THF was added 10.0 g of TBCP-Cl to give a homogeneous solution. This TBCP-Cl/PU blend solution (20 g) was uniformly placed on a 12 cm×12 cm glass plate kept even, and dried at 40° C. for 8 hr under a nitrogen stream and then at 40° C. for 15 hr under reduced pressure to give an about 60 µm thick film (hereinafter this TBCP-Cl/PU blend material is to be referred to briefly as material 23, and the film obtained from the material 23 as film 23). The film 23 contained 20 phr of TBCP-Cl. In the same manner as in Example 1 using film 23, plasma relative coagulation time, antibacterial activity and in vivo antithrombogenicity were determined. Also, material 23 was suspended in THF, and glass beads were coated with this suspension. The hemolytic unit of complement was determined in the same manner as in Example 1. In the same manner as in Example 1, film 23 was subjected to an elution test and the obtained elution film 23' was tested for plasma relative coagulation time and antibacterial activity. The results are shown in Table 1.

Comparative Example 10

To 1000 g of a 5% PU solution in THF was added 10.0 g of TBCP-Cl and 1.00 g of AgZeo to give a homogeneous suspension. This TBCP-Cl,AgZeo/PU blend suspension (20 g) was uniformly placed on a 12 cm×12 cm glass kept even, and dried at 40° C. for 8 hr under a nitrogen stream, which was followed by drying at 40° C. for 15 hr under reduced pressure to give an about 60 µm thick film (hereinafter this TBCP-Cl,AgZeo/PU blend material is to be referred to briefly as material 24, and the film obtained from the material 24 as film 24). The film 24 contained 20 phr of TBCP-Cl and 2 phr of AgZeo. In the same manner as in Example 1 using film 24, plasma relative coagulation time, antibacterial activity and in vivo antithrombogenicity were determined. Also, material 24 was suspended in THF, and glass beads were coated with this suspension. The hemolytic unit of complement was determined by a test similar to that in Example 1. In the same manner as in Example 1, film 24 was subjected to an elution test and the obtained elution film 24' was tested for plasma relative coagulation time and antibacterial activity. The results are shown in Table 1.

Comparative Example 11

Using a PU film (film 25) without organic solvent-soluble heparin or inorganic antibacterial agent, plasma relative coagulation time and antibacterial activity were determined. In the same manner as in Example 1, film 25 was subjected to an elution test and the obtained elution film 25' was tested for plasma relative coagulation time and antibacterial activity. The results are shown in Table 1.

As is evident from the results shown in Table 1, the organic solvent-soluble mucopolysaccharide, antibacterial antithrombogenic composition and medical material of the present invention have superior antithrombogenicity and antibacterial activity, both of which can be maintained even after elution under physiological conditions. In particular, when blended with an organic polymer material, the durability against elution was improved.

In Comparative Examples 1–4 wherein ammonium was used instead of phosphonium, the materials and films showed poor antibacterial activity and poor antithrombogenicity. In Comparative Examples 5–7 wherein dextran sulfate was used instead of heparin, the materials and films showed markedly degraded antithrombogenicity.

The organic solvent-soluble mucopolysaccharide, and the antibacterial antithrombogenic composition and medical material both containing the same, of the present invention, can easily impart antithrombogenicity and antibacterial property to a polymer to be a base material, which properties being maintained not only immediately after preparation of the material but also after long-term elution. Thus, the organic solvent-soluble mucopolysaccharide and antibacterial antithrombogenic material of the present invention show superior applicability as a material to impart antithrombogenicity and antibacterial property to medical materials.

In addition, the antibacterial antithrombogenic composition and medical material of the present invention containing an organic solvent-soluble mucopolysaccharide and an antibacterial agent exhibit long-term antithrombogenicity, have wide antibacterial spectrum and exhibit superior antibacterial activity.

What is claimed is:

1. An organic solvent-soluble ionic complex of at least one mucopolysaccharide and a quaternary phosphonium.

2. The organic solvent-soluble ionic complex of claim 1, wherein the mucopolysaccharide is selected from the group consisting of heparin and heparin derivatives.

3. The organic solvent-soluble ionic complex of claim 1, wherein the quaternary phosphonium has the formula (I)

wherein $R^1$, $R^2$ and $R^3$ are the same or different and each is alkyl having 1 to 12 carbon atoms, aryl having 6 to 12 carbon atoms or aralkyl having 7 to 20 carbon atoms, and $R^4$ is alkyl having 1 to 25 carbon atoms.

4. An antibacterial antithrombogenic composition comprising the organic solvent-soluble ionic complex of any one of claims 1 to 3 and an organic polymer material.

5. The composition of claim 4, wherein the organic polymer material is selected from the group consisting of poly(vinyl halide), poly(vinylidene halide), polyurethane, polyurethaneurea, polyester and polyamide.

6. An antibacterial antithrombogenic composition comprising the organic solvent-soluble ionic complex of any one of claims 1 to 3, an organic polymer material and an antibacterial agent.

7. The composition of claim 6 wherein the organic polymer material is selected from the group consisting of poly(vinyl halide), poly(vinylidene halide), polyurethane, polyurethaneurea, polyester and polyamide.

8. The composition of claim 6 wherein the antibacterial agent is an inorganic antibacterial agent.

9. The composition of claim 8 wherein the inorganic antibacterial agent is at least one member selected from the group consisting of silver zeolite, silver zirconium phosphate complex, silver ceramics, silver silica and antibacterial glass.

10. The composition of claim 8 which comprises 0.1–50 parts by weight of the organic solvent-soluble mucopolysaccharide and 0.1–50 parts by weight of the inorganic antibacterial agent, both relative to 100 parts by weight of the organic polymer material.

11. An antibacterial antithrombogenic composition comprising the organic solvent-soluble ionic complex of any one of claims 1 to 3 and an antibacterial agent.

12. The composition of claim 11 wherein the antibacterial agent is an inorganic antibacterial agent.

13. The composition of claim 12 wherein the inorganic antibacterial agent is at least one member selected from the group consisting of silver zeolite, silver zirconium phosphate complex, silver ceramics, silver silica and antibacterial glass.

14. A medical material comprising the organic solvent-soluble ionic complex of any one of claims 1 to 3.

15. A medical material comprising the organic solvent-soluble ionic complex of any one of claims 1 to 3 and an organic polymer material.

16. A medical material comprising the organic solvent-soluble ionic complex of any one of claims 1 to 3, an organic polymer material and an antibacterial agent.

17. A method for imparting antibacterial property and antithrombogenicity to a medical material, which comprises admixing the organic solvent-soluble ionic complex of any one of claims 1 to 3 with the medical material.

18. A method for imparting antibacterial property and antithrombogenicity to a medical material, which comprises coating the medical material with the organic solvent-soluble ionic complex of any one of claims 1 to 3.

19. A method for imparting antibacterial property and antithrombogenicity to a medical material, which comprises admixing an antibacterial antithrombogenic composition comprising the organic solvent-soluble ionic complex of any one of claims 1 to 3 and an organic polymer material with the medical material.

20. A method for imparting antibacterial property and antithrombogenicity to a medical material, which comprises coating the medical material with an antibacterial antithrombogenic composition comprising the organic solvent-soluble ionic complex of any one of claims 1 to 3 and an organic polymer material.

21. A method for imparting antibacterial property and antithrombogenicity to a medical material, which comprises admixing an antibacterial antithrombogenic composition comprising the organic solvent-soluble ionic complex of any one of claims 1 to 3, an organic polymer material and an antibacterial agent with the medical material.

22. A method for imparting antibacterial property and antithrombogenicity to a medical material, which comprises coating the medical material with an antibacterial antithrombogenic composition comprising the organic solvent-soluble ionic complex of claims 1 to 3, an organic polymer material and an antibacterial agent.

* * * * *

UNITED STATES PATENT AND TRADEMARK OFFICE
CERTIFICATE OF CORRECTION

PATENT NO. : 5,783,570
DATED : July 21, 1998
INVENTOR(S) : Yokota et al.

It is certified that error appears in the above-identified patent and that said Letters Patent is hereby corrected as shown below:

ON THE TITLE PAGE: Item

[56] References Cited: "4,273,873  6/1981  Takagi et al." should read --4,273,873  6/1981  Sugitachi et al.--.

Under "Other Publications", 1st column, line 3: "chem-" should read -- Chem- --.

Under "Other Publications", 2nd column, line 9: "Poilymeric" should read --Polymeric--.

In Column 6, line 46: "According" should begin a new paragraph.

In Column 9, line 18: "coagulate. after" should read --coagulate after--.

In Column 15, line 11: "antithrombo-genicity" should read --antithrombogenicity--.

Signed and Sealed this

Eighth Day of December, 1998

*Attest:*

*Attesting Officer*

BRUCE LEHMAN

*Commissioner of Patents and Trademarks*